(12) United States Patent
Yegorova

(10) Patent No.: US 6,440,410 B1
(45) Date of Patent: Aug. 27, 2002

(54) **REDUCING OXYSTEROLS WITH EXTRACTS OF *MORINDA CITRIFOLIA*, RED WINE, PRUNE, BLUEBERRY, POMEGRANATE, APPLE AND ENZYMES**

(75) Inventor: Inna Yegorova, Northridge, CA (US)

(73) Assignee: A. Glenn Braswell, Miami, FL (US)

( * ) Notice: Subject to any disclaimer, the term of this patent is extended or adjusted under 35 U.S.C. 154(b) by 0 days.

(21) Appl. No.: 09/994,843

(22) Filed: Nov. 28, 2001

Related U.S. Application Data

(62) Division of application No. 09/764,300, filed on Jan. 19, 2001.

(51) Int. Cl.$^7$ .................. A61K 38/54; A61K 38/47; A61K 35/78; A61K 38/48; C12N 9/14
(52) U.S. Cl. .............. 424/94.2; 424/94.61; 424/94.63; 424/725; 424/732; 424/735; 424/765; 424/766; 435/201; 435/209; 435/219
(58) Field of Search .................. 424/725, 94.1, 424/735, 94.2, 94.61, 94.63, 766, 734, 765; 514/783; 435/201, 209, 219

(56) References Cited

PUBLICATIONS

Inhibitory Effect of Flavonoids on Low–Density Lipoprotein Peroxidation Catalyzed by Mannalian 15–Lipoxygenase, da Silva, et al., Filed–Nov. 8, 1999, issued Feb. 23, 2000, Iubmb Life, 49: 289–295.
Inhibition of Mammalian 15–Lipoxygenase–Dependent Lipid Peroxidation in Low–Density Lipoprotein by Quercetin and Quercetin Monoglucosides, da Salva, et al., Jul. 10, 1997, vol. 349, No. 2. Article No. BB970455, issued Jan. 15, pp. 313–320.
Alcohol, free radicals and antioxidants, Puddey, et al., Novartis Foundation Symposium 216, pp. 51–67
Insights Into the Pathogenesis and Prevention of Coronary Artery Disease, O'Keefe, et al., Mayo Clin Proc 1995; 70:69–79.
American Journal of Kidney Diseases, vol. 35, No. 2, Feb.–2000, Noni Juice *(Morinda citrifolia)*Hidden Potential for Hyperkalemia, Mueller, et al., pp. 310–312.
Arteriosclerosis, Thrombosis, and Vascular Biology, vol. 17, No. 10, Oct.–1997, Monounsaturated and Polyunsaturated n–6 Fatty Acid–Enriched Diets Modify LDL Oxidation and Decrease Human Coronary Smooth Muscle Cell DNA Synthesis, Mata, et al.
Antioxidant activity of polyphenolics in diets Rate constants of Reactions of Chlorogenic acid and Caffeic acid with reactive species of oxygen and nitrogen, Kono, et al., Nov.–1996, vol. 1335, pp. 335–342.

Association of Serum Vitamin Levels, LDL Susceptibility to Oxidation, and Autoantibodies against MDA–LDL with Carotid Atherosclerosis, Iribarren, et al., Aug. 21, 1996, vol. 17, No. 6, Jun. 1997, 73–7120(SP) ISSN 1079–5642, pp. 1171–1177.
Iakovieva, et al., 61(3) Eksp.Klin, FarmaKol. 32–4, 1998.
Archives of Internal Medicine, Flavonoid intake and Long–Term Risk of Coronary Heart Disease and Cancer in the Seven Countries Study, Hertog, et al., Feb. 27, 1995, vol. 155, pp. 381–386.
The American Journal of Clinical Nutrition, May 1997, vol. 65, No. 5, Antioxidant flavonols and ischemic heart disease in a Welsh population of men: The Caerphilly Study 1–3, Hertog, et al., 65:1489–94.
Atherosclerosis, Official Journal of the European Atherosclerosis Society, Affiliated with the International Atherosclerosis Society, vol. 137, Apr. 1998, ISSN: 0021–9150, Suppl Sl–S124, Brugge, LDL Oxidation: Therapeutic perspectives, Heller, et al.
Free Radicals in Biology & Medicine, Kelvin J. A. Davies, Ph.D, vol. 2, No. 3, 1986, Intracellular Proteolytic Systems may Function as Secondary Antioxidant Defenses: An Hypothesis, HSC–PSC 614–616, pp. 155–173.
Planta Medica, vol. 57, Jun. 1991, pp. 203–298, Choi, et al., Improvement of Hyperglycemia in Streptozotocin–Diabetic Rats by a Methanolic Extract of *Prunus davidiana* Stems and its Main Component, Prunin. E 21 804 F.
Journal of Natural Products, Jan.–Feb., 1991. vol. 54, No. 1, CODEN JNPRDF 54 (1) 1–327, ISSN: 0163–3864, Antihyperlipidemic Effect of Flavonoids from *Prunus Davidiana*, Jae Sue Chio, Pusan 608–023, pp. 218–224.
Polyphenolic Flavonoids Inhibit Macrophage–Mediated Oxidation of LDL and Attenuate Atherogenesis, Atherosclerosis 137, 1998, S45–S50, Aviram, et al.
Clinical Nutrition, May 2000, vol. 71, No. 5, ISSN 0002–9165, Pomegranate juice consumption reduces oxidative stress, atherogenic modifications to LDL, and platelet aggregation: Studies in humans and in Atherosclerotic Apolipoprotein E–Deficient Mice 1,2. Aviram, et al., Am J Clin Nutr 2000; 71:1062–76.
World Review of Nutrition and Dietetics, vol. 24, 1976, Wld Rev. Nutr. Diet., pp. 117–191, The Flavonoids. A Class of Semi–Essential Food Components: Their Role in Human Nutrition, Joachim Kühnau.

*Primary Examiner*—David M. Naff
*Assistant Examiner*—Mike Meller
(74) *Attorney, Agent, or Firm*—Sierra Patent Group, Ltd.

(57) ABSTRACT

Compositions and methods are provided for reducing oxysterol buildup in the blood and normalizing cholesterol and blood pressure, in a mammal. The compositions comprise *Morinda citrifolia* extract, red wine extract, prune extract, blueberry extract, pomegranate extract, apple extract, and an enzyme mixture.

23 Claims, No Drawings

REDUCING OXYSTEROLS WITH EXTRACTS OF *MORINDA CITRIFOLIA*, RED WINE, PRUNE, BLUEBERRY, POMEGRANATE, APPLE AND ENZYMES

This application is a divisional of U.S. patent application Ser. No. 09/764,300, filed Jan. 19, 2001.

FIELD OF THE INVENTION

The present invention relates to compositions and methods for reducing oxysterols in the blood and normalizing cholesterol and blood pressure in a mammal, by the administration of phytochemicals with antioxidant properties found in fruits and vegetables, including polyphenols.

BACKGROUND OF THE INVENTION

The heart operates similar to a pulsatile pump, in that blood enters the arteries intermittently with each heart beat, causing pressure pulses in the arterial system. In a healthy circulatory system, the pressure at the height of a pulse (systolic pressure) is approximately 120 mm Hg and the pressure at the lowest point of the pulse (diastolic pressure) is approximately 80 mm Hg. The difference between these two pressures, 40 mm Hg, is termed the pulse pressure (Guyton and Hall, TEXTBOOK OF MEDICAL PHYSIOLOGY 221 ($6^{th}$ ed., W. B. Saunders Company, 1956) (1981)). Stroke volume output of the heart and compliance of the arterial system are the two most important factors in pulse pressure.

Atherosclerosis, which is the principal cause of death in Western countries, decreases arterial compliance by depositing calcified plaques on arterial walls, thereby reducing the elasticity of arterial walls. When this occurs, systolic pressure increases greatly, while diastolic pressure, the pressure that causes blood to be transferred from the arteries to the veins, is decreased greatly (Guyton at 221). Thus, blood becomes backed-up in the system, due to the inability of blood to flow through the arteries efficiently, as well as, the inability of blood to flow back to the heart. One key process of artherosclerosis is the accumulation of lipids resulting in distribution of atheromatous plaque. As plaque accumulates in the inner artery wall, the restricted artery is weakened, bulging with cholesterol and toxic deposits. Eventually, the plaque blocks the arteries and interrupts blood flow to the organs they supply. Thus, hyperlipidemia (elevated levels of lipids), and specifically, hypercholesterolemia (elevated levels of cholesterol) are major risk factors for atherosclerosis.

It is known that there are three forms of cholesterol: very low-density lipoprotein (VLDL), low-density lipoprotein (LDL) and high-density lipoprotein (HDL). Arterial wall cholesterol, and therefore atherosclerotic plaque, consists almost exclusively of LDL (Brown and Goldstein, 52 ANN. REV. BIOCHEM. 223 (1983)). Overwhelming evidence shows that LDL cholesterol becomes harmful only in its oxidized form known as oxysterol (Schwartz et al., 71 AM. J. CARDIOL. 9B-14B (1993); Jialal and Grundy, 669 ANN. N. Y. ACAD. SCI. 237–48 (1992)). HDL on the other hand, has been found to be inversely associated with coronary artery disease (Rader, 83(9B) AM. J. CARDIOL. 22F-4F (1999)). It has been determined that for every 1 percent increase in the HDL cholesterol level, the risk of having a coronary event is decreased 3 percent. There are two generally accepted approaches to preventing CVD. The first is to lower LDL cholesterol levels and/or increase HDL cholesterol levels and the other is to reduce levels of oxidized cholesterol.

Several studies have demonstrated that lowering LDL cholesterol levels reduces death from heart disease. The Scandinavian Simvastatin Survival Study followed 4,444 men and women with a history of angina or heart attack over 5.4 years (344 LANCET 1383–1389 (1994)). The study showed that simvastatin, a cholesterol lowering drug, was effective at lowering LDL and thus decreasing deaths and the need for bypass and angioplasty surgery. The Cholesterol and Recurrent Events Trial demonstrated that pravastatin, another cholesterol lowering drug, was effective at lowering LDL cholesterol by 28%, heart attacks by 25%, and strokes by 28%. The study involved 4,158 men and women with a recent history of heart attack (Sacks et al., 335 N. ENGL. J. MED. 1001–1009 (1996)).

A host of LDL cholesterol lowering drugs is currently on the market. The most widely used lipid-lowering drugs include simvastatin (Zocor®), pravastatin (Pravachol®), lovastatin (Mevaco®), fluvastatin (Lescol®), atorvastatin (Lipitor®), and cerivastatin (Baycol®), which make up the group of HMG-CoA reductase inhibitors known as statins. The statins inhibit one of the enzymes responsible for manufacturing VLDL in the liver (HMG-CoA reductase). In response to a lower level of VLDL, the liver removes LDL from the bloodstream to compensate for the loss of VLDL, thereby reducing LDL cholesterol levels in the blood. Statins have also been found to increase HDL levels in some patients. Although effective, the statins are associated with several side effects including reversible liver enzyme elevations, gastrointestinal upset, headache, dizziness, mild skin rashes, muscle pain and muscle inflammation at high does. Moreover, serious liver toxicity is possible. Side effects notwithstanding, recent coronary angiography trials have revealed that if LDL cholesterol can be lowered below 100 mg/dl using cholesterol lowering drugs, atherosclerosis progression is arrested in only 50% to 60% of patients. Alternative cholesterol lowering drugs include: (1) fibrates, gemfibrozil (Lopid®) and clofibrate (Atromid-D®), which activate the enzyme lipoprotein lipase, resulting in a lowering of triglycerides and possibly VLDL; and (2) bile acid sequestrants, better known as resins, cholestyramine (Questran®) and colestipol (Colestid®), which binds and removes bile acids in the intestines. The liver requires cholesterol to make more bile acids and therefore removes LDL from the blood for this function. Fibrates and resins have not found widespread use because the former is associated with hepatitis and a two-fold increased risk of gallstones and the later is associated with gastrointestinal discomfort and an increase in triglycerides, another CHD risk factor. An analysis of several studies even showed a slight increase in overall deaths due to the use of fibrates (Farmer and Gotto, 11(5) DRUG SAF. 301–9 (1994); Grundy 70(21) AM. J. CARDIOL. 271–321 (1992); 40(1030) MED. LETTER DRUGS THER. 68–9 (1998)).

An additional approach to preventing CVD is the reduction of blood triglyceride level. Most fats eaten in food or converted from carbohydrates exist in the form of triglycerides. Hypertriglyceridemia, i.e., elevated blood triglyceride level, is a well known risk factor for coronary heart disease (Ginsberg et al., 78 Med. Clin. North Am. 1 (1994). The fibrates described above are the most effective drug for lowering triglyceride level but is only moderately effective for lowering LDL. Combination drug therapy has thus become more popular in recent years.

It has now been generally accepted that LDL cholesterol becomes harmful only in its oxidized form (Schwartz et al., supra; Jialal and Grundy, supra). Native LDL consists of phospholipids, triglycerides, cholesterol, both free and as an ester, fatty acids (50% of which is polyunsaturated), proteins and lipophilic antioxidants that protect the polyunsaturated fatty acids (PUFA) in cholesterol against free radical attack and oxidation. The first step in the oxidation of cholesterol is the production of free radicals, which are generally induced by oxidative stress. These radicals act to deplete lipids of their natural antioxidants, such as vitamin E and carotinoids, and are also highly reactive against proteins, DNA, PUFA and lipids. Once the natural antioxidants are depleted, the free radicals move to oxidize unprotected LDL. The oxidized cholesterol molecule is recognized by scavenger receptors and internalized by macrophages in the form of lipid loaden foam cells, the first step in the formation of artherosclerotic plaque (Esterbauer et al., 38 ADV. PHARMACOL. 425–56 (1997); Esterbauer, 2 NUTR. METAB. CARDIOVASC. DIS. 55–7 (1992)). Oxidative stress may occur when formation of reactive oxygen species increases, scavenging of reactive oxygen species or repair of oxidatively damaged macromolecules decreases, or both. Thus, factors such as exposure to environmental pollutants and pesticides can instigate the generation of oxysterols internally.

Nutritional aspects of atherosclerosis include the role of antioxidants in the diet such as beta-carotene, selenium, vitamin E, and vitamin C. Fats and cholesterol are very susceptible to free-radical damage and form lipid peroxides as well as oxidized cholesterol when exposed to free radicals. These products of free-radical damage impair artery walls and accelerate the progression of atherosclerosis (MURRAY AND PIZZORNO, ENCYCLOPEDIA OF NATURAL MEDICINE 91 (2nd ed., 1997) (1998)).

Vitamin E has been studied in depth for its effects on cardiovascular disease. For example, studies have shown that supplementation with just 30 IU to 100 IU of vitamin E results in patients having a 41% lower risk of heart disease (MURRAY AND PIZZORNO at 91). Another study showed that supplementation with 100 IU of vitamin E results in reduced progression of coronary artery disease (Id.). Despite these earlier promising results, more recent findings suggest that vitamin E has no effect on foam cell production, although supplementation with vitamin E does indeed increase the levels of vitamin E in cells such as macrophages. The same study concluded that there is a direct correlation between foam cell production and depletion of cellular vitamin E, though this does not correlate with the amount of cell lysis by oxidized LDL (Asmis et al., 20 ARTERIOSCLER. THROMB. VASC. BIOL. 2078–86 (2000)).

More recent efforts towards anti-atherogenic drugs have been directed at compounds with antioxidative properties. Amlodipine, a new calcium antagonist, was determined to normalize elevated levels of oxidized LDL cholesterol without reducing elevated total plasma cholesterol levels. Initial results indicate that atherosclerosis progression was suppressed in monkeys who had been fed an atherogenic diet (Kramsch, 62(Suppl 2) INT. J. CARDIOL. S119–24 (1997)). Monatepil, an alpha 1-adrenoceptor-blocking drug with anti-lipid peroxidation activity was also found to reduce plasma lipid levels (Miyazaki, 7(10 Pt 2) Am. J. HYPERTENS. 131S–40S (1994)).

Polyphenols have been associated with beneficial effects in the prevention of atherosclerosis (Heller et al., 137 ATHEROSCLER. S25–31 (1998)). Many plant phenols and flavonoids contain important dietary antioxidants. It has been speculated that compounds found in red wine or in the Mediterranean diet could explain the "French paradox". This would explain why there is a lower mortality rate due to cardiovascular disease in France and Mediterranean countries, as compared to the other developed countries such as the United States, though the French diet is high in polyunsaturated fats. Id. Substituted phenols and thiophenols have been documented as antioxidant chemicals for inhibiting the peroxidation of LDL cholesterol as well. See U.S. Pat. No. 6,114,572.

Although preventive measures are currently available, a more multi-dimensional approach is needed. A better and natural method for reducing oxysterols in the blood that is readily available and cost-efficient is needed.

SUMMARY OF THE INVENTION

The present invention relates to compositions and methods for reducing oxysterols in the blood and normalizing cholesterol and blood pressure. These compositions preferably comprise Morinda citrifolia extract, red wine extract, prune extract, blueberry extract, pomegranate extract, apple extract, and an enzyme mixture, wherein the enzyme mixture comprises at least one of amylase, cellulase, hemicellulase, and protease. A primary objective of the present invention is the reduction of oxysterols in the blood. Another aspect of the present invention is the administration of a composition that normalizes cholesterol levels in the body. A final aspect of the present invention is the normalizing of blood pressure in the body.

Any and all components of the present compositions preferably range from the minimum effective amount to the maximum effective non-toxic amount. In one preferred embodiment of the present invention, the composition may comprise Morinda citrifolia extract in an amount ranging from about 50 mg to about 150 mg, red wine extract in an amount ranging from about 50 mg to about 150 mg, prune extract in an amount ranging from about 37.5 mg to about 112.5 mg, blueberry extract in an amount ranging from about 25 mg to about 75 mg, pomegranate extract in an amount ranging from about 25 mg to about 75 mg, apple extract in an amount ranging from about 25 mg to about 75 mg, and an enzyme mixture in an amount ranging from about 15 mg to about 45 mg.

In accordance with the present invention, methods and compositions are provided for, inter alia, treating atherosclerosis and its associated diseases including cardiovascular disorders, cerebrovascular disorders, peripheral vascular disorders, and intestinal vascular disorders. The methods and compositions of the present invention are particularly advantageous in that they may be used both to significantly lower plasma cholesterol levels and triglyceride levels and to substantially arrest, reverse and/or cure the arterial plaque deposition and degenerative vascular wall changes associated with atherosclerosis.

The compositions of the present invention can be administered prophylactically, so as to inhibit atherogenesis or restenosis, or therapeutically after CVD or atherogenesis has been diagnosed or initiated. Thus, for example, a patient who is to undergo balloon angioplasty can have a regimen of the composition administered substantially prior to the balloon angioplasty, preferably at least about a week or substantially longer. Alternatively, in a patient where atherogenesis is suspected, administration of the composition can begin at any time. Administration may be accomplished in any manner known to those skilled in the art, including peroral, liposomal, inhalation, sublingual, rectal (e.g., suppositories), or through an oral spray or dermal patch.

Methods are also provided for lowering blood pressure, modulating the production of LDL-cholesterol and reducing the oxidation of LDL into lipid peroxides. As a prophylactic or treatment for atherosclerotic susceptible hosts, the composition is chronically administered at an effective dosage. For restenosis, the agent may be administered for a limited period since this pathological process generally abates about 3 to 6 months after the vascular injury (i.e., angioplasty or atherectomy).

In another aspect, the invention relates to methods of altering the concentration of cholesterol constituents in the blood of a human, to preferably reduce the risk of atherosclerosis and vascular disease, where the composition is administered to a human in an amount effective to increase the concentration of HDL-cholesterol in the blood of the human. Reducing cholesterol levels with the administration of the compositions of the present invention can also prevent other plaque formation and other types of atherosclerotic disease such as the cereberovascular complications of carotid artery plaques, peripheral vascular disease and claudication, and intestinal vascular blockage and infarction.

In another embodiment of the present invention, the composition may be administered to a mammal. Preferably, the mammal is a human. The preparations may be in solid form, for instance, in capsule, powder or granule, or tablet form. Alternatively, the compositions may be dispersed into a suitable liquid. The composition may also be administered orally, preferably two to three times daily.

Another embodiment of the invention involves administering the compositions of the present invention to a human as a material dietary supplement. In yet another embodiment of the invention the composition is administered to a human as a pharmaceutical composition.

DETAILED DESCRIPTION OF THE INVENTION

The present invention relates to the administration of compositions and methods for reducing oxysterols in the blood and normalizing cholesterol and blood pressure. It is understood that the present invention is not limited to the particular methodology, protocols, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the " include plural reference, unless the context clearly dictates otherwise.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the present invention. All references cited herein are incorporated by reference herein in their entirety.

Cardiovascular health may be determined by several parameters: blood pressure; HDL cholesterol level; LDL cholesterol level; triglyceride level and lipid peroxide level. Blood pressure results from a combined force of blood pumping into the arteries and through the circulatory system and the force created as the arteries resist blood flow. In a healthy individual, blood pressure is typically less than 140 mm Hg over 90 mm Hg (see Table 1). The higher number, systolic pressure, represents the pressure while the heart is beating and the lower number, diastolic pressure, is the pressure when the heart is resting between beats (National High Blood Pressure Education Program/National Institutes of Health. The fifth report of the Joint National Committee on Detection, Evaluation, and Treatment of High Blood Pressure. NIH publ. no. 93–1088 (1993)).

TABLE 1

American Heart Association recommended blood pressure levels.

| Blood Pressure Category | Systolic (mm Hg) | | Diastolic (mm Hg) |
|---|---|---|---|
| Optimal | Less than 120 | and | less than 80 |
| Normal | Less than 130 | and | less than 85 |
| High normal | 130–139 | or | 85–89 |
| High Stage 1 (mild) | 140–159 | or | 90–99 |
| High Stage 2 (moderate) | 160–179 | or | 100–109 |
| High Stage 3 (severe) | 180 or higher | or | 110 or higher |

LDL cholesterol level is also indicative of CHD risk. The National Cholesterol Education Program (NCEP) has classified optimal LDL cholesterol level at <100 mg/dL (see Table 2) (269 JAMA 3015–23 (1993); 89 *CIRCULATION* 1329–445 (1994)).

TABLE 2

NCEP classification of Total and LDL-Cholesterol.

| Classification | Total Cholesterol (mg/dL) | LDL-Cholesterol (mg/dL) |
|---|---|---|
| Optimal | <150 | <100 |
| Desirable | 150–199 | 100–129 |
| Mild Hypercholesterolemia | 200–239 | 130–159 |
| Moderate Hypercholesterolemia | 240–299 | 160–219 |
| Severe Hypercholesterolemia | 300 | 220 |

It is recommended that persons with elevated total cholesterol concentrations above 240 mg/dL (6.2 mM/L) receive treatment and that those with borderline values between 200–239 mg/dL (5.2 to 6.2 mM/L) be further evaluated according to the presence of risk factors for coronary artery disease including the sex of the patient, post-menopausal status, a low plasma concentration of HDL cholesterol (below 35 mg/dL [0.9 mM/L]), positive family history, smoking, hypertension and diabetes mellitus (Expert Panel on Detection, Evaluation, and Treatment of High Blood Cholesterol in Adults, 269(23) *J. AM. MED. ASSOC.* 3015–3023 (1993)).

Hypertriglyceridemia has also been cited as a risk factor. The National Cholesterol Education Program classified triglyeride levels as normal (<200 mg/dL), borderline high (200 to 400 mg/dL), high (400 to 1000 mg/dL), and very high (>1000 mg/dL) (National Cholesterol Education Program. Second Report of the Expert Panel on Detection, Evaluation, and Treatment of High Blood Cholesterol in Adults (ATP-11). NIH Publ. No. 93–3095 (1993)). Other factors include obesity, sedentary lifestyle, steroid use, β-adrenergic blocking agents, some diuretics and genetic factors (Frohlich and Pritchard, supra.)

Thus in a preferred embodiment of the invention, administering of the composition of the invention will maintain optimal total, LDL and HDL cholesterol levels and triglycerides level. As previously discussed, lipid peroxidation is an indication of oxidative stress and thus the presence of lipid peroxides have been linked to cardiovascular disease. In another preferred embodiment of the invention, administering of the composition of the invention will increase HDL cholesterol level and reduce elevated triglyceride, LDL cholesterol and lipid peroxide levels.

The components of the compounds of the present invention include the following. *Morinda citrifolia*, also called Noni Juice, has been utilized for the treatment of diabetes, heart trouble, high blood pressure, kidney and bladder disorders, as a poultice, applied to sores and cuts, and as a treatment for bolls. See U.S. Pat. No. 5,288,491. Pomegranate extract, containing phytoestrogens, has been utilized for hormonal replacement associated with menopause. See U.S. Pat. No. 6,060,063. Compositions comprising blueberry extract, which contain plant polyphenols having anti-free radical and antioxidizing properties, have been used to retard the aging process. See U.S. Pat. No. 5,780,060. Compositions comprising apple extract have been used in the reduction of cholesterol as well as weight loss. See U.S. Pat. No. 6,048,532. Similarly, compositions comprising apple extract have been utilized in suppressing cholesterol in the bloodstream. See U.S. Pat. No. 5,510,337. Compositions comprising prune extract have been utilized in the treatment of dermatological conditions such as excema, psoriasis, cold sores, pain, inflammation, osteoarthritis, and rheumatoid arthritis. See U.S. Pat. Nos. 4,564,522 and 5,908,628. Wine grapes have been used to increase blood capillary density, treat atopical dermatitis and haematomas, and treat atherosclerotic damage caused by free-radicals. See U.S. Pat. Nos. 5,665,365 and 5,648,377. Synthetic polyphenols have been used for inhibiting the peroxidation of LDL lipids. See U.S. Pat. No. 6,114,572. Compositions comprising amylase, protease, and hemicellulase have been used to provide controlled release of active agents such as perfumes, pheromones, hormones, vitamins, etc. See U.S. Pat. No. 5,320,837. In addition, dietary supplements devoted to the prevention of cardiovascular disease are well known, such as vitamins and phytochemical supplements, e.g., B-vitamins, folic acid, antioxidants, etc., and have been utilized for reducing the risk of cardiovascular disease. See U.S. Pat. No. 6,054,128.

Components of the novel compositions of the present invention may preferably comprise fruit extracts (such as *Morinda citrifolia* extract, prune extract, blueberry extract, pomegranate extract, and apple extract), red wine extract, and enzymes. In a preferred embodiment, the compositions of the present invention may comprise *Morinda citrifolia* (Noni and Indian Mulberry), in extract form, in amounts preferably ranging from about 50 mg to about 150 mg. *Morinda citrifolia* is an evergreen plant that grows in various parts of the world including Africa, Asia, Australia, and the Americas. Various researchers worldwide have studied *Morinda citrifolia* and its beneficial effects. This research suggests that effects of *Morinda citrifolia* include blood purification, immune system stimulation, cell function regulation, as well as cholesterol level regulation (Levland et al., 36 *PLANTA MED*. 186–7 (1979)). Noni juice, which is made from the fruit of *Morinda citrifolia*, was found in another study to contain 56 mEq/L of potassium, which is similar to the concentration found in both orange juice and tomato juice. Thus, Noni juice may be helpful in the supplementation of potassium, which is known to be important in the maintenance of blood pressure (Mueller et al., 35(2) *AM. J. KIDNEY DIS*. 310–2 (2000)). The leaves of *Morinda citrifolia* comprise high amounts of beta-carotene which has been found to inhibit the oxidation of LDL (Dugas et al., 26(9–10) *FREE RADIC. BIOL. MED*. 1238–44 (1999)). Further, *Morinda citrifolia* contains large amounts of niacin which has been found to convert the easily oxidized LDL into large buoyant oxidation-resistant particles (O'Keefe et al., 70(1) *MAYO CLIN. PROC*. 69–79 (1995)). Finally, *Morinda citrifolia* leaf extracts have been shown to reduce serum lipid concentrations and inhibit the oxidation of LDL (Doi et al., (9) *BIOL. PHARM. BULL*. 1066–71 (2000)). A preferred embodiment of the compositions of the present invention may comprise 100 mg of *Morinda citrifolia* extract. In another preferred embodiment, the *Morinda citrifolia* extract is obtained by extracting the *Morinda citrifolia* fruit with water. In yet another preferred embodiment, the final concentration of the *Morinda citrifolia* extract may be four to one (fruit to water).

Polyphenol is the generic name for a family of compounds that constitute one of the most numerous and ubiquitous groups of plant metabolites. Two subgroups of dietary phenolic compounds, the phenolic acids and flavonoids, have received popular attention due to their high levels in fruits and vegetables (Kuhnau 24 *WORLD REV. NUTR. DIET* 117–91 (1976); Shahidi and Naczk, *FOOD PHENOLICS: SOURCES, CHEMISTRY, EFFECTS, APPLICATIONS* (Technomic Publishing Co) (1995)). Both fruit and red wine extracts contain phenolic antioxidants that have been shown to reduce the risk of cardiovascular disease (Hertog et al., 342 *LANCET* 1007–11 (1993); Hertog et al., 65 *AM. J. CLIN. NUTR*. 1489–94 (1997); Hertog et al., 155 *ARCH. INTERN. MED*. 381–6 (1995)). These polyphenols act as free radical terminators and chelators of metal ions, thereby interfering with lipid peroxidation. In addition, phenoxy radical intermediates are somewhat stable and are unlikely to participate in initiating a new radical chain reaction. In fact, phenoxy radicals intermediates act as terminators of the propagation route by reacting with other free radicals (Shahidi and Wanasundara, 32 *CRIT. REV. FOOD SCI. NUTR*. 67–103 (1992)). Chlorogenic acid and ellagic acid are both polyphenols.

Both prunes and blueberries rank in the top five of an antioxidant assay called ORAC (oxygen radical absorbance capacity) developed by the U.S. Department of Agriculture's Agricultural Research Service (Prior and Cao, 83(4) *J. AOAC INT*. 950–6 (2000)). Prune extract originates from dried fruit of the plum tree. The compositions of the present invention preferably comprise prune, in extract form, in amounts preferably ranging from about 37.5 mg to about 112.5 mg. Prunes, derived from *Prunus davidiana* stems, comprise flavonoid components such as (+)-catechin, prunin (naringenin 7-O-glucoside), and hesperetin 5-O-glucoside, found to produce significant decreases in blood triglyceride and total cholesterol levels in rats (Choi et al., 54(1) *J. NAT. PROD*. 218–24 (1991)). Further studies have shown that Prunus davidiana stems have lowered total lipid levels and blood glucose levels of diabetic rats (Choi et al., 57(3) *PLANTA MED*. 208–11 (1991)). Prune extract comprises significant amounts of monounsaturated fatty acids (MUFAs), which are also prevalent in olive oil. A diet enriched with MUFAs has been found to protect LDL from oxidation, thereby preventing atherosclerosis (Mata et al., 17(10) *ARTERIOSCLER. THROMB. VASC. BIOL*. 2088–95 (1997)). Prunes also contain high amounts of lutein which has been found to inhibit the LDL oxidation. A recent study showed that prunes contain the antioxidant chlorogenic acid, capable of scavenging superoxide anion radicals (Nakatani et al., 48(11) *J. AGRI. FOOD CHEM*. 5512–6 (2000)). A preferred embodiment of the compositions of the present invention may comprise 75 mg of prune extract. In another preferred embodiment, the prune extract comprises at least 60% polyphenols.

The compositions of the present invention may also comprise blueberries, preferably in extract form, in amounts preferably ranging from about 25 mg to about 75 mg. Recent research findings show that blueberries comprise large amounts of antioxidants. The most prominent study concerning antioxidant capabilities of blueberries was completed at Tufts University, where out of approximately 45 fruits and vegetables,. blueberries topped the list in terms of relative quantity of antioxidants. Blueberries also contain high amounts of chlorogenic acid, a widely known antioxidant (Kono et al., 1335(3) *BIOCHIM. BIOPHYS. ACTA* 335–42 (1997); Kono et al., 62(1) *BIOSCI. BIOTECH. BIOCHEM.* 22–7 (1998)). A preferred embodiment of the compositions of the present invention may cormprise 50 mg of blueberry extract. In another preferred embodiment, the blueberry extract comprises at least 16% chlorogenic acid.

The novel compositions of the present invention also may comprise pomegranate, preferably in extract form, in amounts preferably ranging from about 25 mg to about 75 mg. Pomegranates are a rich source of polyphenols as well as other antioxidants. A recent study of human subjects provides evidence that pomegranate juice decreases LDL susceptibility to aggregation and retention and increases the activity of HDL-associated esterase, which protects against lipid peroxidation. This same study found that the uptake of oxidized LDL and native LDL by mouse macrophages were reduced by 20% and atherosclerotic lesions and the number of foam cells were reduced by 44% after supplementation of mice with pomegranate juice (Aviram et al., 71(5) *AM. J. CLIN. NUTR.* 1062–76 (2000)). The bark of pomegranate plants contain ellagic acid, which has been shown to reduce plasma levels of fibrinogen as well as the blood platelet content in rats (Damas et al., 45(2) *THROMB. RES.* 153–63 (1987)). In fact, ellagic acid is a potent antioxidant in vitro (Bagehi et al., 15 *FREE RAD. BIOL. MED.* 217–22 (1993)). A further study concluded that ellagic acid causes a marked antioxidant effect in rats and restores myocardial functions (Iakovleva et al., 61(3) *EKSP. KLIN. FARMAKOL.* 32–4 (1998)). A preferred embodiment of the compositions of the present invention may comprise 50 mg of pomegranate extract. In another preferred embodiment, the pomegranate extract comprises at least 40% ellagic acid and 60% polyphenols.

The compositions of the present invention may comprise apple, preferably in extract form, and preferably in amounts ranging from about 25 mg to about 75 mg. Apples comprise high amounts of polyphenols such as quercetin, a recognized lipoxygenase inhibitor, which was found to inhibit LDL oxidation (Silva et al., 349(2) *ARCH. BIOCHEM. BIOPHYS.* 313–20 (1998)). A similar study found that quercetin inhibited human LDL alpha-tocopherol consumption, which is part of the first stage of LDL oxidation and characterized by the consumption of antioxidants and the subsequent formation of lipid hydroperoxides (Silva et al., 49(4) *IUBMB LIFE* 289–95 (2000)). Apples are also rich in lutein, which has been found to be inversely related to the extent of atherosclerosis in humans (Iribarren et al., 17(6) *ARTERIOSCLER. THROMB. VASC. BIOL.* 1171–7 (1997)). A further study concluded that acarotenoid rich (i.e., lutein, lycopene, alpha-tocopherol) food intake directly correlated with inhibition of LDL oxidation (Hininger et al., 51(9) *EUR. J. CLIN. NUTR.* 601–6 (1997)). Apples also comprise chlorogenic acid, a widely known antioxidant (Kono et al., 1335(3) *BIOCHIM. BIOPHYS. ACTA* 335–42 (1997); Kono et al., 62(1) *BIOSCI. BIOTECH. BIOCHEM.* 22–7 (1998)). A preferred embodiment of the compositions of the present invention may comprise 50 mg of apple extract. In another preferred embodiment, the apple extract comprises at least 60% polyphenols and 5% chlorogenic acid.

In another embodiment, the compositions of the present invention may comprise red wine, preferably in extract form, in amounts preferably ranging from about 50 mg to about 150 mg. Red wine extract comprises polyphenolic compounds which have been found to exhibit a protective effect against atherosclerotic cardiovascular disease in that they inhibit the oxidation of LDL (Puddey et al., 216 *NOVARTIS FOUND. SYMP.* 51–62 (1998)). Another study concluded that polyphenols found in red wine reduces oxidation of LDL by reducing macrophage oxidative states (Aviram et al., 137(Suppl.) *ATHEROSCLER.* S45–S50 (1998); Van Golde et al., 147(2) *ATHEROSCLER.* 365–70 (1999); Serafini et al., 128 *J. NUTR.* 1003–1007 (1998)). A preferred embodiment of the compositions of the present invention may comprise 100 mg of red wine extract. In another preferred embodiment, the red wine extract comprises at least 30% polyphenols.

One of the best-known properties of polyphenolic compounds is their capacity to bind and precipitate protein. Thus, tannins, another group of polyphenols, have been shown to reduce digestibility of protein (Butler, *CHEMISTRY AND SIGNIFICANCE OF CONDENSED TANNINS* 391–402 (Hemingway and Karchesy, eds. Plenum Press) (1989); Longstaff and McNab, 65 *BR. J. NUTR.* 199–216 (1991)). Tannins can also bind digestive enzymes and inhibit them (Quesada et al., 59 *J. FOOD PROT.* 185–92 (1996); Oh and H6ff, 51 *J. FOOD SCI.* 577–80 (1986)). A preferred embodiment of the compositions of the present invention therefore may comprise an enzyme blend to counteract the effects of any polyphenols in the compositions of the present invention. The compositions of the present invention may comprise a mixture of enzymes comprising one or more of amylase, cellulase, hemicellulase, or protease in amounts preferably ranging from about 15 mg to about 45 mg. Amylases catalyze hydrolysis of polysaccharides, cellulases and hemicellulases catalyze hydrolysis of cellulose and hemicellulose, respectively, and proteases catalyze hydrolysis of peptide bonds. The mixture of enzymes found in the compositions of the present invention preferably work together to facilitate the break down of carbohydrates and proteins from the extracts of the present invention. Therefore, the novel enzyme mixtures of the present invention may preferably assist with the digestion and absorption of nutritional supplements. Enzymes, such as amylase, cellulase and hemicellulase from a fungal source have been used to convert ingested insoluble dietary starches and other complex carbohydrates into soluble materials, which can be used in the body as a primary source of energy for athletes see U.S. Pat. No. 5,817,350. Additionally, a recent study showed that when cellulases in solution were sprayed on the forage ration of cows, the cows exhibited increased milk production as well as increased digestion of food versus cows fed a control ration (Lewis et al., 82(3) *J. DAIRY SCI.* 611–7 (1999)). Another study concluded that amylase of germinating cereal grains used in porridge significantly improved energy intake of children suffering from acute diarrhea (Darling et al., 21(1) *J. PEDIATR. GASTROENTEROL. NUTR.* 73–81 (1995)). Supplementary proteases have been shown to aid in digestion (Heinicke et al., 25 *EXP. MED. SURG.* 156–68 (1967)). In addition, research has concluded that proteolytic enzymes may act as secondary antioxidant defenses when primary antioxidants such as vitamin E and beta-carotene are depleted (Davies, 2(3) *J.*

FREE RAD. BIOL. MED. 155–73 (1986)). A preferred embodiment of the compositions of the present invention may comprise 30 mg of the novel enzyme blend. In another preferred embodiment, the enzyme blend comprises one or more of amylase, cellulase, hemicellulase or protease.

As discussed in detail above, in one aspect of the invention, the novel compositions of the present invention preferably comprise: *Morinda citrifolia* extract, red wine extract, prune extract, blueberry extract, pomegranate extract, apple extract, and an enzyme mixture, wherein the enzyme mixture comprises at least one of amylase, cellulase, hemicellulase and protease. Any and all components preferably range from the minimum effective amount to the maximum effective non-toxic amount. In a further preferred embodiment, the composition comprises about 50 mg to about 150 mg of *Morinda citrifolia extract, about* 50 mg to about 150 mg of red wine extract, about 37.5 mg to about 112.5 mg of prune extract, about 25 mg to about 75 mg of blueberry extract, about 25 mg to about 75 mg of pomegranate extract, about 25 mg to about 75 mg of apple extract, and about 15 mg to about 45 mg of an enzyme mixture that comprises one or more of amylase, cellulase, hemicellulase, and protease.

Another aspect of the present invention relates to compositions and methods for reducing the buildup of oxysterols in the blood and normalizing cholesterol and blood pressure, comprising administering to the mammal a composition comprising: *Morinda citrifolia* extract, red wine extract, prune extract, blueberry extract, pomegranate extract, apple extract, and an enzyme mixture, wherein the enzyme mixture comprise at least one of amylase, cellulase, hemicellulase and protease.

In a preferred aspect of the invention, a composition of the present invention is administered to reduce or control blood pressure in persons having a systolic pressure over about 130 mm Hg and/or a diastolic pressure over about 85 mm Hg. In another embodiment of the invention, the compositions are administered to reduce or control blood cholesterol levels in persons having a total cholesterol of about 240 mg/dL (5.95 mmol/L) or higher. In another embodiment of the invention, the compositions are administered to reduce levels of LDL-cholesterol in persons with a LDL-cholesterol of about 130 mg/dL (3.41 mmol/L) or higher. In another embodiment, a composition of the present invention is administered to raise levels of HDL to persons with a HDL-cholesterol of about 35 mg/dL (1.04 mmol/L) or lower to reduce the risk of atherosclerosis associated with low HDL levels. The compositions and methods of the present invention may also be utilized to improve or maintain vascular health in specific organ systems including the cardiovascular system, the cereberovascular system, the peripheral vascular system, and the intestinal vascular system.

In a preferred embodiment of the invention, the present composition is formulated for oral administration. Any dosage form may be employed for providing the patient with a dosage of the present compositions. Dosage forms include tablets, capsules, dispersions, suspensions, solutions, capsules, transdermal delivery systems, etc. Tablets and capsules represent the most advantageous oral dosage unit form. Any method known to those of ordinary skill in the art may be used to prepare capsules, tablets, or other dosage formulations. Tablets or capsules can be coated by methods well known to those of ordinary skill in the art.

According to one aspect of the invention, a composition is provided comprising a pharmaceutically acceptable combination of the composition and at least one carrier. Pharmaceutically acceptable carriers for inclusion into the present compositions include carriers most suitable for combination with lipid-based drugs such as diluents, excipients and the like which enhance its oral administration. Suitable carriers include, but are not limited to, sugars, starches, cellulose and derivatives thereof, wetting agents, lubricants such as sodium lauryl sulfate, stabilizers, tabletting agents, anti-oxidants, preservatives, coloring agents and flavoring agents. Pharmaceutically acceptable carriers include binding agents such as pregelatinized maize starch, polyvinylpryrrolidone or hydroxypropyl methycellulose; binders or fillers such as lactose, pentosan, microcrystalline cellulose or calcium hydrogen phosphate; lubricants such as magnesium stearate, talc or silica; disintegrants such as potato starch or sodium starch; or wetting agents such as sodium lauryl sulfate. Reference may be made to *REMINGTON'S PHARMACEUTICAL SCIENCES*, 17TH ED., 1985, for other carriers that would be suitable for combination with the present compositions. As will be appreciated, the pharmaceutical carriers used to prepare compositions in accordance with the present invention will depend on the administrable form to be used.

According to an additional embodiment, the compositions of the present invention may be admixed by conventional methods and may be administered by an alternative route such as suppository, spray, liquid, powder, liposome, dermal patch, and inhalant. These methods are well known to those skilled in the art. For example, liposomes may be formulated according to methods such as those of U.S. Pat. Nos. 5,853,755, 4,235,871, or 4,708,861 (liposome-gel combination). Sublingual and transdermal methods are also well known to those skilled in the art, e.g., U.S. Pat. No. 5,922,342 describes a sublingual formulation and U.S. Pat. No. 4,997,655 describes a transdermal administration method.

Another embodiment of the invention involves administering the composition of the present invention to a human in one or more tablets as a dietary supplement. In yet another embodiment of the invention, the composition is administered to a human as a pharmaceutical composition.

The administration of the composition is preferably in accordance with a predetermined regimen, which preferably would be at least two to three times daily and may be over an extended period of time as a chronic treatment, and could last for one year or more, including the life of the patient. The dosage administered may, inter alia, depend upon the frequency of the administration, the blood level desired, other concurrent therapeutic treatments, the severity of the condition, whether the treatment is for prophylaxis or therapy, the age of the patient, the levels of LDL-cholesterol and HDL-cholesterol in the patient, and the like.

Other objectives, features and advantages of the present invention will become apparent from the following specific examples. The specific examples, while indicating specific embodiments of the invention, are provided by way of illustration only. Accordingly, the present invention also includes those various changes and modifications within the spirit and scope of the invention that may become apparent to those skilled in the art from this detailed description.

EXAMPLE 1

Composition 1

A composition of the following formulation was prepared in capsule form by standard methods known to those skilled in the art:

| | |
|---|---|
| Morinda citrifolia extract | 100 mg |
| Red wine extract (30% polyphenols) | 100 mg |
| Prune extract (60% polyphenols) | 75 mg |
| Blueberry extract (16% chorogenic acid) | 50 mg |
| Pomegranate extract (40% ellagic acid; 60% polyphenols) | 50 mg |
| Apple extract (60% polyphenols, 5% chorogenic acid) | 50 mg |
| Enzyme blend | 30 mg |

Two to three tablets per day is the recommended dosage for an average weight adult human (70-kg).

Clinical Studies:

A study of the effect of a dietary supplement comprising Morinda citrifolia extract, red wine extract, prune extract, blueberry extract, pomegranate extract, apple extract, and an enzyme mixture, on blood pressure, HDL cholesterol level, LDL cholesterol level, triglyceride level and plasma lipid peroxide level is conducted over a six-month period. Plasma lipid peroxide levels were determined according to the procedure described by Gorog et al., 111(1) ATHEROSCLER. 47–53 (1994). A statistical analysis is performed to compare the resulting blood pressure, HDL cholesterol, LDL cholesterol, triglyceride and plasma lipid peroxide levels of individuals receiving the supplement with a control (placebo) group, to measure the improvement in cardiovascular health from administration of the test preparation.

Sixty adult individuals are selected for inclusion in the statistical study. Two weeks prior to the start of the study, each subject completes a one-week dietary intake record and is interviewed by a Registered Dietitian to calculate each individual's daily energy requirement. Baseline blood pressure, HDL cholesterol, LDL cholesterol, triglyceride and plasma lipid peroxide levels are determined with blood samples drawn on two separate days. Subjects are randomly assigned to one of two treatment groups: the group receiving the test tablets (Composition 1) or the group receiving matching placebo tablets. Both groups continue on their normal diet and incorporate three tablets of either the Composition 1 or placebo in their daily diet.

The effects of supplementing the diet with the above composition are evaluated for blood pressure, HDL cholesterol, LDL cholesterol, triglyceride and plasma lipid peroxide levels using multiple linear regression analysis and a standard students t-test. In each analysis, the baseline value of the outcome variable is included in the model as a covariant. Treatment by covariant interaction effects is tested by the method outlined by Weigel and Narvaez, 12 CONTROLLED CLINICAL TRIALS 378–394 (1991). In the absence of significant interaction effects, the interaction terms are removed from the model. Regression model assumptions of normality and homogeneity residual variance are evaluated by inspection of plots of residuals versus plots of predicted values. Temporal outset of effects is detected sequentially by testing for the presence of significant treatment effects at 18, 12, and 6 weeks, proceeding to the earlier time in sequence only when significant effects have been identified at each later time period. In addition, one-way analysis of variance is compared only when differences exist between groups concerning nutrient intake, physical activity, and body mass index at each time point. Changes from the baseline within each group are evaluated using paired t-tests. Additionally, analysis of variance is performed on all baseline measurements and measurable subject characteristics to assess homogeneity between groups. All statistical procedures are conducted using the Statistical Analysis System (SAS Institute Inc., Cary, N.C.) using an alpha level of 0.05 for all statistical tests.

A statistically significant decrease in blood pressure, LDL cholesterol, triglyceride and plasma lipid peroxide levels and a statistically significant increase in blood HDL cholesterol level are observed in the treated subjects upon completion of the study, but not in the control subjects.

EXAMPLE 2

A study of the effect of the composition comprising Morinda citrifolia extract, red wine extract, prune extract, blueberry extract, pomegranate extract, apple extract, and an enzyme mixture, on blood pressure, HDL cholesterol, LDL cholesterol, triglyceride and plasma lipid peroxide levels, is conducted over a nine-week period. Plasma lipid peroxide levels were determined according to the procedure described by Gorog et al., 111(1) ATHEROSCLER. 47–53 (1994). A statistical analysis is performed to compare plasma lipid peroxide levels of a test group and a control (placebo) group to determine if a significant improvement in blood pressure, HDL cholesterol, LDL cholesterol, triglycenride and plasma lipid peroxide levels results from administration of the test preparation.

Sixty adult individuals with no history or symptoms of heart disease are selected for inclusion in the statistical study. Each patient was held in a clinical setting for a total of nine weeks. A total of three isocaloric diets were imposed, and each patient held on each diet for three weeks. The components of each diet may vary as long as lipid levels in the diet were maintained. The three diets are as follows:

| American Heart Association Diet II | |
|---|---|
| Fat | 25% |
| Cholesterol | 80 mg/1000 kCal |
| Polyunsaturated/saturated fat | 1.5 |
| Average American Diet | |
| Fat | 43% |
| Cholesterol | 200 mg/1000 kCal |
| Polyunsaturated/saturated fat | 0.34 |
| Combination Diet | |
| Fat | 43% |
| Cholesterol | 80 mg/1000 kCal |
| Polyunsaturated/saturated fat | 0.34 |

Subjects are randomly assigned to one of two treatment groups: the group receiving the test tablets (Composition 1) or the group receiving matching placebo tablets. Both groups continue on the lipid-controlled diet and incorporate three tablets of either the Composition 1 or placebo in their daily diet. At the end of each three-week period, blood pressure, HDL cholesterol, LDL cholesterol, triglyceride and plasma lipid peroxide levels are determined.

The effects of supplementing the diet with the above composition are evaluated for blood pressure, HDL cholesterol, LDL cholesterol, triglyceride and plasma lipid peroxide levels using multiple linear regression analysis and a standard students t-test. In each analysis, the baseline value of the outcome variable is included in the model as a covariant. Treatment by covariant interaction effects is tested by the method outlined by Weigel and Narvaez, 12 *CONTROLLED CLINICAL TRIALS* 378–394 (1991). In the absence of significant interaction effects, the interaction terms are removed from the model. Regression model assumptions of normality and homogeneity residual variance are evaluated by inspection of plots of residuals versus plots of predicted values. Temporal outset of effects is detected sequentially by testing for the presence of significant treatment effects at 18, 12, and 6 weeks, proceeding to the earlier time in sequence only when significant effects have been identified at each later time period. In addition, one-way analysis of variance is compared only when differences exist between groups concerning nutrient intake, physical activity, and body mass index at each time point. Changes from the baseline within each group are evaluated using paired t-tests. Additionally, analysis of variance is performed on all baseline measurements and measurable subject characteristics to assess homogeneity between groups. All statistical procedures are conducted using the Statistical Analysis System (SAS Institute Inc., Cary, N.C.) using an alpha level of 0.05 for all statistical tests.

A statistically significant decrease in blood pressure, LDL cholesterol, triglyceride and plasma lipid peroxide levels and a statistically significant increase in blood HDL cholesterol level are observed in the treated subjects upon completion of the study, but not in the control subjects.

The invention has been described in detail with particular reference to preferred embodiment thereof. However, it will be appreciated that those skilled in the art, upon consideration of this disclosure may make variations and modifications within the spirit and scope of the invention.

The disclosure of all publications cited above are expressly incorporated by reference in their entireties to the same extent as if each were incorporated by reference individually.

I claim:

1. A method of reducing oxysterol in the blood stream of a mammal comprising administering to said mammal a composition comprising *Morinda citrifolia* extract, red wine extract, prune extract, blueberry extract, pomegranate extract, apple extract, and an enzyme mixture.

2. The method of claim 1, wherein said red wine extract comprises about 30% polyphenols.

3. The method of claim 1, wherein said prune extract comprises about 60% polyphenols.

4. The method of claim 1, wherein said blueberry extract comprises about 16% chlorogenic acid.

5. The method of claim 1, wherein said pomegranate extract comprises about 40% ellagic acid and about 60% polyphenols.

6. The method of claim 1, wherein said apple extract comprises about 60% polyphenols and about 5% chlorogenic acid.

7. The method of claim 1 wherein said *Morinda citrifolia* extract, is about 50 mg to about 150 mg.

8. The method of claim 1, wherein said red wine extract is about 50 mg to about 150 mg.

9. The method of claim 1, wherein said prune extract is about 37.5 mg to about 112.5 mg.

10. The method of claim 1, wherein said blueberry extract is about 25 mg to about 75 mg.

11. The method of claim 1, wherein said pomegranate extract is about 25 mg to about 75 mg.

12. The method of claim 1, wherein said apple extract is about 25 mg to about 75 mg.

13. The method of claim 1, wherein said enzyme mixture is about 15 mg to about 45 mg.

14. The method of claim 1, wherein said enzyme mixture contains at least one enzyme is selected from the up consisting of amylase, cellulase, hemicellulase, and protease.

15. The method of claim 1, wherein said composition comprises: 100 mg of *Morinda citrifolia* extract, 100 mg of red wine extract, 75 mg of prune extract, 50 mg of blueberry extract, 50 mg of pomegranate extract, 50 mg of apple extract, and 30 mg of an enzyme mixture.

16. The method of claim 15, wherein said enzyme mixture contains at least one enzyme is selected from the group consisting of amylase, cellulase hemicellulase, and protease.

17. The method of claim 1, wherein said composition is delivered in a pharmaceutically acceptable carrier.

18. The method of claim 1, wherein said composition is administered 2 to 3 times daily.

19. The method of claim 18, wherein said administering is selected from the group consisting of oral, inhalation, sublingual, rectal and dermal.

20. The method of claim 18, wherein said composition is administered orally.

21. The method of claim 1, wherein said composition is provided in a form selected from the group consisting of a gel cap an emulsion, rectal suppositories, oral spray, dermal patch and liposome.

22. The method of claim 1, wherein said composition is in solid form selected from the group consisting of a tablet and a capsule.

23. The method of claim 1, wherein said mammal is a human.

* * * * *